US006733752B1

(12) United States Patent
Greene et al.

(10) Patent No.: US 6,733,752 B1
(45) Date of Patent: May 11, 2004

(54) PREVENTION OF TUMORS WITH MONOCLONAL ANTIBODIES AGAINST *NEU*

(75) Inventors: Mark I. Greene, Penn Valley, PA (US); Makoto Katsumato, Bryn Mawr, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 08/525,800

(22) PCT Filed: Mar. 30, 1994

(86) PCT No.: PCT/US94/03528
§ 371 (c)(1),
(2), (4) Date: Nov. 20, 1995

(87) PCT Pub. No.: WO94/22478
PCT Pub. Date: Oct. 13, 1994

(51) Int. Cl.$^7$ .............................................. A61K 39/395
(52) U.S. Cl. ................................ 424/130.1; 424/133.1; 424/141.1; 424/155.1; 424/156.1; 350/387.1; 350/387.3; 350/387.7; 350/388.1
(58) Field of Search ........................... 424/133.1, 130.1, 424/141.1, 155.1, 156.1; 530/350, 387.1, 387.3, 387.7, 388.1, 388.8, 388.85

(56) References Cited

U.S. PATENT DOCUMENTS 4,444,744 A    4/1984  Goldenberg ................. 424/1.1
5,165,922 A   11/1992  Hellstrom et al. ........... 424/85.8

FOREIGN PATENT DOCUMENTS

WO    WO 94/00136    1/1994

OTHER PUBLICATIONS

Qian, X et al. In: Encyclopedia of Cancer, vol 2: 835–856, 1997.*
Dorland's Illustrated Medical Dictionary, p. 1254, 1985.*
Muller, W.J. Cell, 54: 105–115, 1988.*
Kim, J. P., Ann Surgery 216 (3): 269–79; 278–279, 1992.*
Yu, D et al. Oncogene 6(11): 1991–1996, 1991.*
Adams, JM et al Science, 254 (5035): 1161–1167, 1991.*
Mulshine, JL. et al, Chest 103(1): S4–S11, 1993.*
Drebin, J.A. et al. 1986 PNAS, USA, 83: 9129–9133.
Drebin, J.A. et al. 1988, Oncogene 2: 273–277.
Osband, M.E. et al. 1990 Immunol. Today 11: 193–195.
Queen, C. et al. 1989, PNAS, 86: 10029–10033.
Bach, J.F. et al., "Safety and Efficacy of Therapeutic Monoclonal Antibodies in Clinical Therapy", *Immunology Today* 1993, 14, 421–425.
Beretta, G. and Luporini, "Chemotherapy Versus Immunotherapy in the Treatment of Human Solid Tumors", in "From Oncogenes to Tumor Antigens", Giraldo, G. et al., eds., Elsevier Science Publishers, Amsterdam, 1985, pp. 227–238.

Bouchard, L. et al., "Stochastic Appearance of Mammary Tumors in Transgenic Mice Carrying the MMTV/*c–neu* Oncogene", *Cell* 1989, 57, 931–936.
Ceriani, R.L. and Blank, "An Experimental Model for the Immunological Treatment of Breast Cancer", in *Proceedings of the International Workshop on Monoclonal Antibodies and Breast Cancer* 1984, pp. 248–268.
Drebin, J.A. et al., "Development of Monoclonal Antibodies Reactive with the Product of the *neu* Oncogene", in "Immunology and Cancer", Kripke, M.L. and Frost, eds., University of Texas Press, Austin TX, p. 277.
Drebin et al., *Symposium on Fundament./Cancer Res.* 1986, 38, 277–289.
Drebin, J.A. et al., "Monoclonal Antibodies Identify a Cell–Surface Antigen Associated with an Activated Cellular Oncogene", *Nature* 1984, 312, 545–548.
Drebin, J.A. et al., "Down–Modulation of an Oncogene Protein Product and Reversion of the Transformed Phenotype by Monoclonal Antibodies", *Cell* 1985, 41, 695–706.
Drebin, J. et al., "Monoclonal Antibodies Reactive With Distinct Domains of the *neu* Oncogene–encoded p185 Molecule Exert Synergistic Ant–Tumor Effects", *Oncogene* 1988, 2, 273–277.
Drebin, J. et al., "Inhibition of Tumor Growth by a Monoclonal Antibody Reactive with an Oncogene–encoded Tumor Antigen", *PNAS USA* 1986, 83, 9129–9133.
Harris et al., *Tibtech* 1993, 11, 42–44.
Hudson, L. and Hay, "Practical Immumology", Blackwell Scientific Publications, London, p. 117.
Lodato et al., "Immunohistochemical Evaluation of c–erB–2 Oncogene Expression in Ductal Carcinoma *in Situ* and Atypical Ductal Hyperplasia of the Breast", *Modern Pathol.* 1990, 3(4), 449.
Muller, W.J. et al., "Single–Step Induction of Mammary Adenocarinoma in Transgenic Mice Bearing the Activated *c–neu* Oncogene", *Cell* 1988, 54, 105–115.
Osband, M. and Ross, "Problems in the Investigational Study and Clinical Use of Cancer Immunotherapy", *Immunol. Today* 1990, 11, 193–195.

(List continued on next page.)

*Primary Examiner*—Anthony C. Caputa
*Assistant Examiner*—Minh Tam Davis
(74) *Attorney, Agent, or Firm*—Darby & Darby

(57) ABSTRACT

Prevention of transformation of a normal cell into a tumour cell in an individual at risk of developing a tumour having tumours which have p185 on their surfaces comprises: (a) identifying the individual and (b) administering to the individual an antibody which specifically binds to p185. Also claimed is a method of preventing transformation of a normal cell into a tumour cell that has p185 on its surface in an individual who has had a tumour that has p185 on its cell surfaces removed or who has had a cancer characterised by tumour cells that have p185 on their surfaces enter remission, comprising (a) identifying the individual and (b) administering to the individual an antibody which specifically binds to p185.

17 Claims, No Drawings

OTHER PUBLICATIONS

Sefton et al., "Comparison of the Expression of the src Gene of Rous Sarcoma Virus In Vitro and In Vivo", *Virology* 1978, 28, 957–971.

Sugita, K. et al., "Use of a Cocktail of Monoclonal Antibodies And Human Complement in Selective Killing of Acute Lymphocytic Leukemia Cells", *Int. J. Cancer* 1986, 37, 351–357.

Vitetta, E. et al., "Redesigning Nature's Poisons to Create Anti–Tumor Reagents", *Science* 1987, 238, 1098–1104.

Queen, C. et al., "A Humanized Antibody that Binds to the Interleukin 2 Receptor", *PNAS USA* 1989, 86, 10029–10033.

* cited by examiner

PREVENTION OF TUMORS WITH MONOCLONAL ANTIBODIES AGAINST NEU

This application is a 371 of PCT/US 94/03528, file on Mar. 30, 1994.

FIELD OF THE INVENTION

The invention relates to methods of preventing the transformation of normal mammalian cells into tumor cells.

BACKGROUND OF THE INVENTION

Huge amounts of time and money have been spent to better understand cancer and searching for ways to prevent and cure cancer. The results of these research efforts have provided a greater understanding of the biological and biochemical events that participate in the formation of tumors.

Tumor cells display a variety of characteristics that distinguish them from normal cells. Recent studies in the molecular genetics of cancer indicate that certain genes known as oncogenes may play a role in the transformation of some cells from their normal condition to a cancerous condition.

An oncogene which encodes a protein that exposes antigenic sites on the surface of transformed cells has been identified by transfection of DNA from ethyl nitrosourea-induced rat neuroblastomas into NIH3T3 cells. This oncogene has been termed neu. The neu gene has been found to be amplified in some human tumors, particularly those of the breast, suggesting that this gene may play a role in the etiology of human cancer.

The neu oncogene encodes a cell surface protein on rat cells transformed by it. The protein encoded by the neu oncogene is a 185 kDa transmembrane glycoprotein with tyrosine kinase activity, generally known by the name p185. The neu gene is closely related to the epidermal growth factor (EGF) receptor gene in structure.

The neu oncogene and p185 have also been found active in human adenocarcinomas including breast, lung, salivary gland and kidney adenocarcinomas, as well as prostate neuroblastoma. In human primary breast cancers, amplification of the neu oncogene was found in about 30% of all malignant tumors examined. Increased stage of malignancy, characterized by large tumor size and increased number of positive lymph nodes as well as reduced survival time and decreased time to relapse, was directly correlated with an increased level of amplification of the neu gene. The neu protooncogene is expressed at low levels in normal human tissues. Further, neu has been associated with 100% of the ductal carcinomas studied in situ, Lodato, R. F., et al. (1990) *Modern Pathol.* 3(4):449.

While changes in diet and behavior can reduce the likelihood of developing cancer, it has been found that some individuals have a higher risk of developing cancer than others. Further, those individuals who have already developed cancer and who have been effectively treated face a risk of relapse and recurrence.

Advancements in the understanding of genetics and developments in technology as well as epidemiology allow for the determination of probability and risk assessment an individual has for developing cancer. Using family health histories and/or genetic screening, it is possible to estimate the probability that a particular individual has for developing certain types of cancer. Those individuals that have been identified as being predisposed to developing a particular form of cancer can take only limited prophylactic steps towards reducing the risk of cancer. There is no currently available method or composition which can chemically intervene with the development of cancer and reduce the probability a high risk individual will develop cancer.

Similarly, those individuals who have already developed cancer and who have been treated to remove the cancer or are otherwise in remission are particularly susceptible to relapse and reoccurrence.

There is a need for improved preventative agents for individual with a high risk to develop cancer and for individuals who have had cancer enter remission or be removed. In cases where the type of cancer the individual is at risk to develop, such as tumors associated with neu, there is a need for specific agents which can be administered to reduce the probability that a predisposed individual will develop cancer or that a patient in remission will suffer a relapse.

SUMMARY OF THE INVENTION

The present invention provides methods for the prevention of tumor cells which express a translation product of the neu oncogene on their surfaces. In accordance with the invention, a prophylactic amount of an antibody that specifically binds to p185 is administered to an individual.

The present invention provides methods of preventing the transformation of normal human cells into tumors cells which express a translation product of the neu oncogene on their surfaces. In accordance with the invention, a prophylactic amount of an antibody that specifically binds to p185 is administered to an individual.

The present invention provides methods for the prevention of the origination of genetically induced mammalian tumor cells which express a translation product of the neu oncogene on their surfaces by interfering with a transforming event. In accordance with the invention, a prophylactic amount of an antibody that specifically binds to p185 is administered to an individual.

DETAILED DESCRIPTION OF THE INVENTION

As used herein, the terms "neu-associated cancer" and "neu-associated tumors" are meant to refer to tumor cells and neoplasms which express the neu gene to produce p185.

The translation product of the neu oncogene is p185, a transmembrane glycoprotein having tyrosine kinase activity and a molecular weight of about 185,000 daltons as determined by carrying out electrophoresis on the glycoprotein and comparing its movement with marker proteins of known molecular weight. Experiments have shown that administration of an antibody binding to p185 results in the reduced incidence of neu-associated tumors in a population susceptible to such tumors. Anti-p185 antibodies selectively inhibit the neoplastic development in animals susceptible to developing neu transformed tumors.

The occurrence of mammalian tumors cells which express a translation product of the neu oncogene on their surfaces can be prevented by administration of antibodies which bind to p185. In accordance with the invention, a prophylactic amount of an antibody that specifically binds to p185 is administered to an individual who is identified as being susceptibleto neu-associated tumors.

The present invention is particularly useful to prophylactically treat an individual who is predisposed to develop neu-associated tumors or who has had neu-associated tumors and is therefore susceptible to a relapse or recurrence.

As used herein, the term "high risk individual" is meant to refer to an individual who has had a neu-associated tumor either removed or enter remission and who is therefore susceptible to a relapse or recurrence. As part of a treatment regimen for a high risk individual, the individual can be prophylactically treated against the neu-associated tumors that they have been diagnosed as having had in order to combat a recurrence. Thus, once it is known that an individual has had cancer characterized by tumor cells with p185 on their cell surfaces, the individual can be treated according to the present invention to prevent normal cells from transforming into tumor cells.

Prophylactic compositions for prevention of neu-associated tumors comprise an antibody specific for the p185 molecule and a pharmaceutically acceptable carrier. According to preferred embodiments, the prophylactic compositions for prevention of neu-associated tumors are injectable. The compositions comprise an antibody specific for the p185 molecule and a pharmaceutically acceptable carrier or injection vehicle.

The antibodies are chosen from antibodies made according to the procedures described in detail below or other conventional methods for producing monoclonal antibodies. The carrier be selected from those well known to persons having ordinary skill in the art. An example of a carrier is sterile saline.

Antibodies Specific for Rat and Human p185

Those having ordinary skill in the art can produce monoclonal antibodies which specifically bind to p185 and are useful in prophylactic anti-tumor compositions using standard techniques and readily available starting materials. The techniques for producing monoclonal antibodies are outlined in Harlow, E. and D. Lane, (1988) *ANTIBODIES: A Laboratory Manual*, Cold Spring Harbor Laboratory, Cold Spring Harbor N.Y., which is incorporated herein by reference, provide detailed guidance for the production of hybridomas and monoclonal antibodies which specifically bind to target proteins.

Briefly, the protein of interest, rodent or human p185 for example, is injected into mice. The spleen of the mouse is removed, the spleen cells are isolated and fused with immortalized mouse cells. The hybrid cells, or hybridomas, are cultured and those cells which secrete antibodies are selected. The antibodies are analyzed and, if found to specifically bind to the protein of interest, the hybridoma which produces them is cultured to produce a continuous supply of antigen specific antibodies.

According to the present invention, antibodies specific for either rodent, particularly rat, p185 or the corresponding human p185 may be used in prophylactic compositions. Accordingly, either rodent p185 or human p185 is used to generate hybridomas. In both cases, the genes which encode these proteins are widely known and readily available to those having ordinary skill in the art. Thus, one having ordinary skill in the art can make antibodies useful to practice the present invention. In addition to rodent antibodies, the present invention relates to human antibodies, humanized antibodies, Fabs and chimeric antibodies and Fabs which bind to p185 which may be produced routinely by those having ordinary skill in the art.

In some preferred embodiments of the present invention, the prophylactic composition comprises monoclonal antibodies designated 7.5.5, 7.9.5, 7.16.4 and 7.21.2. In some preferred embodiments of the present invention, the prophylactic composition comprises humanized monoclonal antibodies or Fabs which contain complementarity determining regions from antibodies designated 7.5.5, 7.9.5, 7.16.4 and 7.21.2. In some preferred embodiments of the present invention, the prophylactic composition comprises humanized monoclonal antibodies or Fabs which contain variable regions from antibodies designated 7.5.5, 7.9.5, 7.16.4 and 7.21.2.

Patient Population

Although the present invention may be used to prevent tumors in any patient population identified as being susceptible to neu-associated tumors, it is particularly useful in high risk individuals who, for example, have a family history of neu-associated cancer or show a genetic predisposition. Additionally, the present invention is particularly useful to prevent neu-associated tumors in patients who have had neu-associated tumors removed by surgical resection or who have been diagnosed as having neu-associated cancer in remission.

Those having ordinary skill in the art can readily identify individuals who are susceptible to neu-associated tumors, particularly those individuals considered to be a high risk for whom the methods of the invention are particularly useful.

Compositions

The prophylactic compositions may include additional components to render them more effective. For example, a prophylactic composition of the invention may comprise multiple anti-p185 antibodies including antibodies specific for different epitopes of p185.

The prophylactic compositions may include other anti-cancer agents such as, for example, cis-platin. As a step in the method of the invention, chemotherapeutics may be administered prophylactically to patients who have treated for neu-associated cancer by surgery or radiation treatment and who have had removal or remission.

Administration Regimen

About 5 $\mu$g to 5000 mg of antibody may be administered. In some preferred embodiments, 50 $\mu$g to 500 mg of antibody may be administered. IN other preferred embodiments, 500 $\mu$g to 50 mg of antibody may be administered. In a preferred embodiment, 5 mg of antibody is administered.

Prophylactic compositions may be administered by an appropriate route such as, for example, by oral, intranasal, intramuscular, intraperitoneal or subcutaneous administration. In some embodiments, intravenous administration is preferred.

Subsequent to initial administration, individuals may be boosted by readministration. In some preferred embodiments, multiple administrations are performed.

EXAMPLES

Example 1

Mice

C3H and [C3H×DBA/2] f1 (C3D2 f1) mice were obtained from the Jackson Laboratory, Bar Harbor, Me. Inbred congenitally athymic Balb/c nude (nu/nu) mice were obtained from the National Cancer Institute animal colony (San Diego, Calif.). Animals used in the experiments are maintained in accordance with the guidelines of the Committee on Care and Use of Laboratory Animals of the Institute of Animal Resources, National Research Council (DHEW publication number (NIH) 78-23, revised 1978).

Isolation of Hybridomas That Secrete Monoclonal Antibodies That are Reactive With Neu-transformed Cells C3H/HeJ mice are repeatedly immunized with NIH 3T3 transfectants transformed by the neu oncogene (cell line B1041-1-1), emulsified in Freund's adjuvant. Spleens from immune mice are fused with the aminopterin-sensitive NS-1 myeloma line, and hybridomas are selected in hypoxanthine-aminopterin-thymidine media. Culture supernatants from growing hybridomas are initially screened for the presence of antibody capable of binding B104-1-1 cells by indirect immunofluorescence using fluorescence activated cell sorting (FACS). Positive supernatants are then tested for specificity by determining whether they contain antibody capable of binding normal NIH 3T3 cells, or NIH 3T3 cells transformed by transfection with Harvey sarcoma virus proviral DNA (cell line XHT-1-1a).

Isotype Analysis of Monoclonal Antibodies

The heavy chain isotypes of the monoclonal antibodies characterized here are determined by double immunodiffusion in agar according to the method of Ouchterlony, in Hudson, L and F. C. Hay, eds., *Practical Immunology*, Blackwell Scientific Publications, London, p.117, which is specifically incorporated herein.

Purification of Monoclonal Antibodies

Hybridoma cells are washed several times in HBSS and injected into pristine primed, 400 rad irradiated, C3D2f1 mice to induce ascites fluid production. When the mice develop significant ascites, the fluid is removed by aspiration with a 19 gauge needle and hybridoma cells and debris are removed by centrifugation at 1000 xg. The clarified ascites fluid is then stored at −70° C. prior to purification, or is purified immediately. Purification is performed according to the method of Drebin et al. in *Immunology and Cancer*(M. L. Kripke and P. Frost, eds.) University of Texas Press, Austin, Tex., p. 277 which is specifically incorporated herein.

Specificity of Antibodies

Flow Cytometry

Cells are removed from dishes with buffered EDTA (Versene; Gibco) and washed twice in FACS medium (Hank's balanced salt solution(HBBS; Gibco) supplemented with 2% fetal calf serum (FCS), 0.1% sodium azide and 10 mM HEPES); $1 \times 10^6$ cells in 0.1 ml FACS medium are incubated with 0.1 ml of hybridoma culture supernatant for 1 hr at 4° C. Cells are washed twice with FACS medium, and incubated with 0.1 ml fluorescein isothiocyanate (FITC)-conjugated rabbit-anti-mouse immunoglobulin (Miles) diluted 1:50 in FACS medium for 1 hr at 4° C. Cells are then washed twice in FACS medium and fixed in 2% paraformaldehyde-phosphate-buffered saline (PBS). Samples are run on an Ortho 2150 Cytofluorograph using the logarithmic amplifier. Each sample contains 10,000 cells per sample.

Cyanogen Bromide Coupling of Antibodies to Sepharose Beads

CNBr-activated Sepharose 4B beads are swollen in 1 mM HCl, and then mixed with purified antibodies in coupling buffer (0.5 M NaCl, 0.1 M NaHCO$_3$, pH 8.3) at a ratio of 2 mg immunoglobulin (1 mg per ml) per ml of activated beads. The mixture is rotated overnight on an end-over-end mixture at 4° C., and then unreacted sites are blocked with 0.2 M glycine pH 8.0 for 2 hours at room temperature. The beads are then poured onto a sintered glass filter and washed with three cycles of 100 bead volumes of coupling buffer, 10 bead volumes of 3.5 M MgCl$_2$, 100 bead volumes of coupling buffer to wash away excess adsorbed proteins. Non-specific protein binding to the antibody coupled beads is blocked by a brief wash in sterile DMEM containing 10% fetal calf serum. The beads are then washed in PBS and stored in PBS containing 0.1% sodium azide at 4° C. until they are used in immunoprecipitation experiments. All of the monoclonal antibodies which specifically bind to the surface of neu-transformed cells are reactive with the p-185 molecule encoded by the neu oncogene. These monoclonal antibodies specifically precipitate p185 from metabolically labeled lysates of neu-transformed cells.

Immunoprecipitation of p185 From Metabolically Labeled b104-1-1 cell lysates

For labeling with $^{35}$S-cysteine $10^6$ cells are seeded in 100 mm culture dishes and labelled for 18 hr in 2 ml minimal essential medium (MEM) containing 0.1 the usual amount of cysteine, 2% dialyzed fetal calf serum and 500 µCi $^{35}$S-cysteine (77 Ci mmol$^{-1}$; NEN). For labeling with $^{32}$P, $3 \times 10^5$ cells are seeded in 60-mm tissues culture dishes and incubated for 18 hr in 0.8 ml phosphate-free Dulbecco-Vogt modified Eagle's medium containing 4% fetal calf serum and 0.4 mCi $^{32}$P (carrier-free; NEN). Cells are lysed in phosphate-buffered RIPA buffer containing 1 mM ATP, 2 mM EDTA and 20 mM sodium fluoride, and immunoprecipitates are prepared and washed according to Sefton et al. (1979) *Virology* 28:957–971 (1979), which is specifically incorporated herein. One third of each lysate is incubated with 1 µl of normal mouse serum or 60×concentrated 7.16.4 culture supernatant at 4° C. for 60 min. Sheep anti-mouse immuinoglobulin (1 µl; Cappel) is added to each sample and incubation continued for 30 min. Immune complexes are pelleted using fixed Protein A-bearing Staphylococcus aureus and washed. Samples are analyzed by SDS-polyacrylamide gel electrophoresis in 7.5% acrylamide—0.17% bis-acrylamide gels. The gels are treated for fluorography and exposed to preflashed Kodak X-Omat AR film for 10 days.

Antibodies Specific for Human neu Oncogene

Rat and human neu oncogene DNA sequences are similar and the two genes share some sequences as can be shown by computer-aided analysis of the structure of the genes. Antibodies to the human gene can be produced by following the procedure as set forth above for making antibodies to the rat neu oncogene and using the rat neu oncogene sequences which are shared with human neu oncogene instead of the rat neu oncogene.

As a result of competitive binding studies, antibody 7.16.4 was found to bind to domain 1, antibodies 7.5.5, 7.9.5 and A11 were found to bind to domain 2, and antibody 7.21.2 was found to bind to domain 3. The denominations of domains 1, 2, and 3 are arbitrary and are used as a short hand to group antibodies that competitively bind to p185 into the same group. Antibodies placed into any one group competitively bind with other antibodies of the same group to p185, but do not to any substantial extent inhibit binding of antibodies to other portions of p185.

Isotype analysis of the antibodies provided the following isotypes for the antibodies: IgG1-antibody 7.9.5; IgG2a-antibodies A11 and 7.16.4; IgG2B-antibody 7.5.5; and IgG1-antibody 7.21.2.

Hybridoma cell line producing monoclonal antibody 7.9.5 was deposited in the American Type Culture Collection, 10801 University Boulevard, Manassas, Va. 20110-2209 on Jul. 3, 1990 and has accession number HB10492. Hybridoma cell line producing monoclonal antibody 7.16.4 was deposited in the American Type Culture Collection, 10801 University Boulevard, Manassas, Va. 20110-2209 on Jul. 3, 1990 and has accession number HB 10493.

Example 2

Oncogenic rat neu (neuT) differs from wild type neu by a point mutation within the transmembrane domain of the coding sequence. Certain strains of transgenic mice that express the neuT oncogene (L. Bouchard, et al. *Cell* 57, 931 (1989)) develop breast tumors at an average of forty four weeks of age. Intraperitoneal injection of a monoclonal antibody against p185$^{neuT}$ dramatically affected tumor development in these transgenic mice. A significant proportion (50%) of mice did not develop tumors even after ninety weeks of age when injected with monoclonal antibodies. This demonstrates for the first time that immunological manipulations of p185$^{neuT}$ can effectively prevent the development of genetically induced breast tumors in a rodent model.

In the transgenic mouse models of human breast adenocarcinomas developed by L. Bouchard et al. (*Cell* 57, 931 (1989) and by W. J. Muller et al. (*Cell* 54, 105 (1988)), the neuT oncogene under the transcriptional control of the murine mammary tumor virus (MMTV) long terminal repeat leads to mammary tumors.

In one of these models, female transgenic mice developed multiple mammary adenocarcinomas asynchronously, between 20 and 45 weeks of age (comparable to human middle age) in a stochastic manner. The histologic features and metastatic potential of these adenocarcinomas resembled tumors seen in humans. This transgenic mouse model has certain important characteristics; 1) the expressed oncogene is genetically programmed and is activated in a predictable manner in conjunction with tissue specific promoter/enhancer elements; 2) the stochastic appearance of tumors suggests that involvement of other oncogenes or oncogenic factors is necessary for full development of tumors, a situation clearly analogous to naturally occurring tumors; and 3) the immunological interactions between the tumors and the host transgenic animal can be examined, since the host immune system was intact. Finally, the effect of distinct treatments could be assessed on tumors prior to or after their predicted development.

In the present set of experiments we have employed only female mice of line MN-10 on the BALB/c background. These mice became pregnant frequently and were able to nurse their litters during the treatment period.

To determine the effects of MAb specific for the ectodomain of p185$^{neuT}$ on the development of breast tumors, two groups of transgenic mice with different dosages of antibodies starting at 6 weeks of age were treated. One group of transgenic mice was injected intraperitoneally with 10 μg of MAb 7.16.4 in 100 μl of phosphate buffered saline (PBS) biweekly (low dose group). Another group of transgenic mice was injected with the same amount of MAb 7.16.4 twice weekly (high dose group). Each group of mice had comparable numbers of control transgenic mice treated with injections of PBS only. An isotype matched MAb (IgG2a) known to have no effect on p185$^{neuT}$ transformed cells in vitro or in vivo was used as a control.

As expected, two groups of control transgenic mice (n=12 and n=10) developed tumors between 28.0 and 72.0 weeks of age. The average tumor onset periods of these two sets of control mice were 42.8±3.2 (SEM) and 45.0±3.0 weeks, respectively. The group of mice receiving low doses of MAb 7.16.4 (n=11) developed tumors between 31.0 and 75.0 weeks of age with the average tumor onset period 50.7±2.7 weeks. Although the average tumor onset period was significantly delayed by 7.9 weeks between the low dosage group and its associated control mice (p<0.05), the difference between the low dosage group and the second control mice (5.7 weeks delay) was marginally insignificant (0.05<p<0.1). There was no significant difference between the two controls (0.1<p).

The high dose treatment group of mice developed tumors after 45.6 weeks of age. However, 6 of 12 mice in this group (50%) remained free of tumors at more than 90 weeks of age. This indicates that treatment of transgenic mice with MAb 7.16.4 10 μg twice weekly can effectively suppress tumor development in a large fraction of these mice for almost their entire life span (about 100 weeks). Nearly half of the mice in both control groups and in the low dosage groups developed two to five independent tumors within a six week period after the first tumor became visible. In contrast, all animals that developed malignancy in the high dosage group had only a single tumor. The tumor volume of the high dosage group at a given point after tumor appearance was always smaller than that of control mice at the same point.

The histology of the MMTV/neuT transgenic mice used in the present experiment have been previously characterized in detail (L. Bouchard et al. *Cell* 57, 931 (1989)) which is incorporated herein by reference. All untreated mice developed moderately to poorly differentiated ductal adenocarcinomas of the breast. A small proportion of these mice also developed salivary gland and Harderian gland tumors consistent with previous observations. The breast tumors which arose in mice treated with MAb 7.16.4 were moderately to poorly differentiated adenocarcinomas (FIG. 2A and B) which were histologically indistinguishable from that of untreated mice. Occasionally single tumors displayed both poorly and moderately differentiated areas. The non-tumor breast tissue of the high dosage treated mice was histologically similar to that of the untreated mice, even after 70 weeks of treatment No ductal epithelial hyperplasia, ductal destruction or lymphoid infiltration was observed. There is no indication that the suppression of tumor development in MAb treated mice involves host immune mechanisms such as antibody-dependent cellular cytotoxicity (ADCC). Similarly, studies using tumor implant model of MAb therapy found no decisive contribution of host immune elements to the elimination of established tumors expressing neuT.

About 30% of human breast tumors show p185$^{c-erB-2}$ overexpression, usually associated with gene amplification, and it is relevant that the overexpression of p185$^{c-erbB-2}$ can be observed in early stages of human breast tumors. The data indicates that continuous down-regulation of the p185$^{neuT}$ molecule leads to tumor growth suppression in a dose-dependent manner. The antibody mediated dose-dependent tumor suppression shown here suggests that the continuous down-regulation of p185$^{neuT}$ diminishes the activity of necessary oncogenic factors in tumorigenesis. Prevention of metastasis or recurrence is feasible by administering anti-p185 antibodies.

What is claimed is:

1. A method of inhibiting development into breast cancer cells of breast cells that overexpress p185 in an individual in need of such inhibition which comprises administering to said individual an antibody which competes with an antibody produced by cell line ATCC Deposit No. 10493 for binding to p185 and specifically binds to p185 in sufficient amount to down regulate the overexpressed p185 and inhibit the development of said breast cells that overexpress p185 into breast cancer cells.

2. The method of claim 1 wherein the antibody has the complementarity determining regions from an antibody produced by a cell line ATCC Deposit No. HB10493.

3. The method of claim 1 wherein the antibody has the variable regions from an antibody produced by a cell line ATCC Deposit No. HB 10493.

4. The method of claim 1 wherein the antibody is produced by a cell line ATCC Deposit No. HB 10493.

5. The method of claim 1 wherein the antibody is a humanized antibody.

6. The method of claim 5 wherein the antibody is a humanized antibody with complementarity determining regions from the antibody produced by ATCC Deposit No. HB10493.

7. The method of claim 5 wherein the antibody is a humanized antibody with variable regions from the antibody produced by ATCC Deposit No. HB10493.

8. The method of claim 1 further comprising administering to said individual a second antibody which specifically binds to p185.

9. The method of claim 1 further comprising administering to said individual an anti-tumor agent.

10. The method of claim 1 wherein said individual is a human.

11. The method of claim 10 wherein the antibody is the antibody produced by ATCC Deposit No. HB 10493.

12. The method of claim 10 wherein the antibody is a humanized antibody.

13. The method of claim 10 further comprising administering to said individual a second antibody which specifically binds to p185.

14. The method of claim 10 further comprising administering to said individual an anti-tumor agent.

15. The method of claim 9, wherein the anti-tumor agent is cis-platin.

16. The method of claim 14, wherein the anti-tumor agent is cis-platin.

17. The method of claim 1 wherein said antibody binds to an epitope bound by the antibody produced by cell line ATCC Deposit No. 10493.

* * * * *

UNITED STATES PATENT AND TRADEMARK OFFICE
CERTIFICATE OF CORRECTION

PATENT NO. : 6,733,752 B1
DATED : May 11, 2004
INVENTOR(S) : Mark I. Greene et al.

It is certified that error appears in the above-identified patent and that said Letters Patent is hereby corrected as shown below:

Title page,
Item [75], Inventors, "Makoto Katsumato" should read -- Makoto Katsumata --.
Item [56], References Cited, U.S. PATENT DOCUMENTS, after "5,165,922 A", insert -- * --.
OTHER PUBLICATIONS,
"Drebin, J.A. et al." reference, after "9133." insert -- * --; and after "277." insert -- * --.
"Osband, M.E. et al." reference, after "195." insert -- * --.
"Queen C. et al." reference, after "10033." insert -- * --.
"Hudson, L. and Hay," reference, delete "Immumology" and substitute -- Immunology --.
"Muller, W.J. et al.," reference, delete "Adenocarinoma" and substitute
-- Adenocarcinoma --.
Add the following:
-- The Basic Science of Oncology, Second Edition, Tannock, I.F., et al. (eds.), McGraw-Hill, Inc., New York, pp. 144-145 (1992);

Lodato, R.G., et al., Mod. Pathol., 3:449 (1990) [ABSTRACT ONLY]

Xu, R., et al., Mod. Pathol., 16:116 (2002) [ABSTRACT ONLY]

Stark, A., et al., J. Clin. Oncol., 18:267-274 (2000)

Liu, S., et al., Proc. Natl. Acad. Sci. USA, 99:3770-3775 (2002)

Montagna, C., et al., Oncogene, 21:890-898 (2002)

Shackney, S.E., et al., Cytometry, 29:1-27 (1997)

Tomaszewska, R., et al., Pol. J. Pathol., 49:83 (1998) [ABSTRACT ONLY]

Siegel, P.M., et al., EMBO J., 8:2149-2164 (1999)

Zhang et al., (1999) "Shared Antigenic Epitopes and Pathobiological Functions of Anti-p185her2/neu Monoclonal Antibodies", Expt. and Mol. Pathology, 67:15-25

Zhang et al., (2003) "Therapeutic Monoclonal Antibodies for the ErbB Family of Receptor Tyrosine Kinases", Cancer Biol. & Therapy, 2(Suppl.):90-94

Wolpoe et al., (2003) "HER-2/neu-Specific Monoclonal Antibodies Collaborate with HER-2/neu-Targeted Granulocyte Macrophage Colony-Stimulating Factor Secreting Whole Cell Vaccination to Augment CD8+ T Cell Effector Function and Tumor-Free Survival in Her-2/neu-Transgenic Mice", J. Immunol., 171:2161-942169 --.

UNITED STATES PATENT AND TRADEMARK OFFICE
CERTIFICATE OF CORRECTION

PATENT NO. : 6,733,752 B1
DATED : May 11, 2004
INVENTOR(S) : Mark I. Greene et al.

It is certified that error appears in the above-identified patent and that said Letters Patent is hereby corrected as shown below:

Column 1,
Line 4, delete "file" and substitute -- filed --.
Line 5, after "1994", insert -- , which is a continuation-in-part of serial no. 08/038,498, filed 03/30/1992, abandoned. --.

Column 3,
Line 62, delete "susceptibleto" and substitute -- susceptible to --.

Column 4,
Line 36, delete "IN" and substitute -- In --.
Line 52, delete "f1 (C3D2 f1 )" and substitute -- F1 (C3D2 F1) --.
Line 65, delete "B1041-1-1)" and substitute -- B104-1-1) --.

Column 5,
Line 18, delete "C3D2f1" and substitute -- C3D2F1 --.
Line 23, delete "1000 xg" and substitute -- 1000 x g --.

Column 6,
Line 21, delete "immuinoglobulin" and substitute -- immunoglobulin --.

Column 7,
Line 11, delete "(1989)" and substitute -- (1989)) --.

Column 8,
Line 6, delete "groups" and substitute -- group --.
Lines 60, 62 and 65, after "by" delete "a".

Signed and Sealed this

Twenty-fourth Day of January, 2006

JON W. DUDAS
*Director of the United States Patent and Trademark Office*

UNITED STATES PATENT AND TRADEMARK OFFICE
CERTIFICATE OF CORRECTION

PATENT NO. : 6,733,752 B1  Page 1 of 1
APPLICATION NO. : 08/525800
DATED : May 11, 2004
INVENTOR(S) : Mark I. Greene et al.

It is certified that error appears in the above-identified patent and that said Letters Patent is hereby corrected as shown below:

On title page
Item [75], Inventors, add -- Jeffrey Drebin --.

Signed and Sealed this

Twenty-sixth Day of February, 2008

JON W. DUDAS
*Director of the United States Patent and Trademark Office*